(12) United States Patent
Wang

(10) Patent No.: US 11,340,147 B2
(45) Date of Patent: May 24, 2022

(54) SOUND WAVE HOMOGENIZING MODULE AND BIOLOGICAL SAMPLE PREPARATION SYSTEM

(71) Applicant: ZINEXTS LIFE SCIENCE CORP., New Taipei (TW)

(72) Inventor: Chun-Chao Wang, New Taipei (TW)

(73) Assignee: ZINEXTS LIFE SCIENCE CORP., New Taipei (TW)

( * ) Notice: Subject to any disclaimer, the term of this patent is extended or adjusted under 35 U.S.C. 154(b) by 333 days.

(21) Appl. No.: 16/630,842

(22) PCT Filed: Jul. 13, 2017

(86) PCT No.: PCT/CN2017/092819
§ 371 (c)(1),
(2) Date: Jan. 13, 2020

(87) PCT Pub. No.: WO2019/010677
PCT Pub. Date: Jan. 17, 2019

(65) Prior Publication Data
US 2020/0141840 A1    May 7, 2020

(51) Int. Cl.
*G01N 1/00*        (2006.01)
*G01N 1/28*        (2006.01)
*C12N 15/10*       (2006.01)

(52) U.S. Cl.
CPC ......... *G01N 1/286* (2013.01); *C12N 15/1003* (2013.01); *G01N 2001/2866* (2013.01)

(58) Field of Classification Search
None
See application file for complete search history.

(56) References Cited

U.S. PATENT DOCUMENTS

2013/0206857 A1* 8/2013 Ivri .................... B05B 17/0669
239/4

* cited by examiner

*Primary Examiner* — Jyoti Nagpaul

(57) ABSTRACT

Disclosed herein are a sonic homogenizing module (100, 200, 300) and a biological sample preparation system (500) containing the same. The sonic homogenizing module (100, 200, 300) comprises a rod made of a magnetic material (120, 220, 320); a piezoelectric conductor (130, 230,330); a driver (140, 340); and a sleeve-coupling member (110, 210, 310) having a first portion defining a space (112, 212, 312) for coupling with a gripper module of a biological sample preparation system, and for accommodating the piezoelectric conductor and the driver therein; and a second portion having a conduit (114, 214, 314) for receiving the rod therethrough; wherein the driver (140, 340) is electrically coupled with the piezoelectric conductor (130, 230,330) and is configured to drive the piezoelectric conductor (130, 230, 330) to generate a sonic vibration at a frequency of 100 KHz-1 MHz.

11 Claims, 7 Drawing Sheets

SOUND WAVE HOMOGENIZING MODULE AND BIOLOGICAL SAMPLE PREPARATION SYSTEM

This application is a 35 U.S.C. § 371 National Phase Entry Application of International Patent Application No. PCT/CN2017/092819, filed Jul. 13, 2017, which designates the U.S., the contents of which is incorporated herein by reference in their entirety.

BACKGROUND OF THE INVENTION

1. Field of the Invention

The present disclosure relates in general, to the field of nucleic acid extraction. More particularly, the present disclosure relates to extracting nucleic acids via use of a biological preparation system equipped with a sonic homogenizing module disclosed herein.

2. Description of Related Art

Existing automated nucleic acids extraction apparatus isolates or extracts nucleic acids with the aid of magnetic beads, in which nucleic acids released from the lysed biological samples are adsorbed onto the silica coated outer surface of the magnetic beads, thereby allowing the nucleic acids to be easily separated or extracted from the sample. For the purpose of thorough mixing, a rod is used to move up and down in the sample vial to stir and mixed the lysed biological sample with the suspended magnetic beads therein. However, this mixing act (i.e., repeatly moving the rod up and down in the sampling well) per se inevitably causes the splash of the content in the sampling well, leading to cross-contamination, and consequently an erroneous result. Accordingly, existing automated nucleic acids extraction apparatus is designed to operate in a relatively larger volume sample, so as to keep the fluctuation of the liquid surface in the sample well to the minimum.

In view of the foregoing, there exists in this art a need of an improved method and or device to facilitate the preparation of a biological sample while reducing the chance of cross-contamination.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

One aspect of the present disclosure aims to provide a sonic homogenizing module, which integrates the sonic and/or ultrasonic technology to mix the contents in a sampling well of any typical biological sample preparation system. In the present system, the mixing is achieved at less volume of a sample and by use of high frequency sonic vibration, while at the same time greatly reduces the risk of cross-contamination commonly associated with existing biological sample preparation system.

According to embodiments of the present disclosure, the sonic homogenizing module comprises, a rod made of a magnetic material; a piezoelectric conductor; a driver; and a sleeve-coupling member having a first portion defining a space for coupling with the gripper module of the biological sample preparation system, and for accommodating the piezoelectric conductor and the driver therein; and a second portion having a conduit for receiving the rod there through; wherein the driver is electrically coupled with the piezoelectric conductor and is configured to drive the piezoelectric conductor to generate a sonic vibration.

According to embodiments of the present disclosure, the piezoelectric conductor is configured to generate sonic vibration at a frequency ranging from 100 KHz to 1 MHz.

According to optional embodiments of the present invention, the sonic homogenizing module may further comprise a vibration motor disposed in the space of the first portion.

According to optional embodiments of the present invention, the sonic homogenizing module may further comprise a sleeve removably fitted on and around the outer surface of the rod extending out of the conduit of the second portion of the sleeve-coupling member.

According to some embodiments of the present disclosure, the piezoelectric conductor in the space of the first portion is adjacent to the conduit.

According to some embodiments of the present disclosure, the space of the first portion extends into the second portion of the sleeve-coupling member, allowing the piezoelectric conductor accommodated in the space of the first portion to be disposed in a manner that it surrounds the conduit of the second portion.

The second aspect of the present invention is to provide a biological sample preparation system, which comprises at least one of the sonic homogenizing module described above; and a gripper module electrically coupled thereto. The gripper module is configured to move the sonic homogenizing module to a pre-designated position.

According to one embodiment of the present invention, the biological sample preparation system further comprises a sample plate, which has a plurality of sampling wells, in which the content in each well is mixed via sonic vibration generated by the present sonic homogenizing module.

This summary is provided to introduce a selection of concepts in a simplified form that are further described below in the detail description. This summary is not intended to identify key features or essential features of the claimed subject matter, nor is it intended as an aid in determining the scope of the claimed subject matter.

The details of one or more embodiments of this disclosure are set forth in the accompanying description below. Other features and advantages of the invention will be apparent from the detail descriptions, and from claims.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF PREFERRED EMBODIMENTS

Figure 1A:
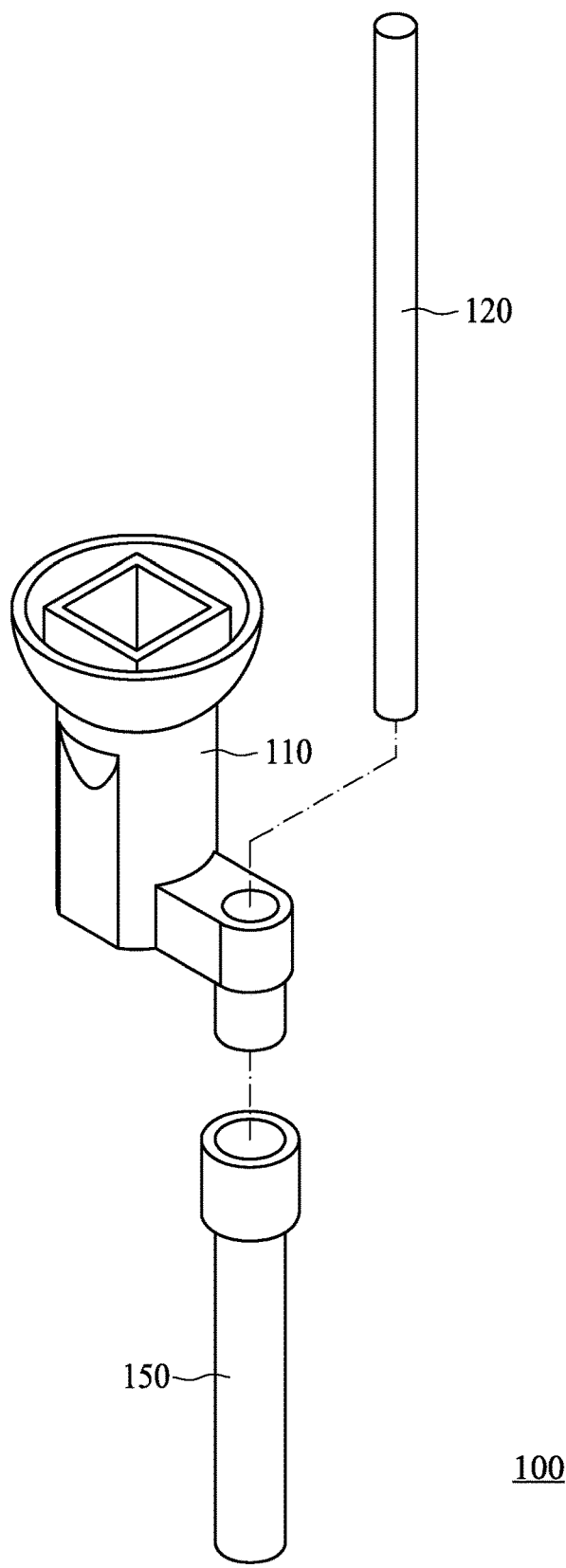
FIGS. 1A and 1B are schematic diagrams respectively illustrating a sonic homogenizing module 100 before and after assembling with a sleeve 150 in according with one embodiment of the present disclosure.

The detailed description provided below in connection with the appended drawings is intended as a description of the present disclosure and is not intended to represent the only forms in which the present disclosure may be constructed or utilized. The description sets forth the functions of the example and the sequence of steps for constructing and operating the example. However, the same or equivalent functions and sequences may be accomplished by different examples.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "molecules" as used herein refers to nucleic acids and/or proteins in a biological sample.

The term "biological sample" as used herein refers to biological samples or specimens suitable for extracting nucleic acids therefrom by any of the conventional biological sample preparation system, as well as the sonic homogenizing module and/or system comprising the same disclosed herein. Examples of the biological samples suitable for extracting nucleic acid therefrom include, but are not limited to, blood, body fluid, animal tissue, plant tissue, eukaryotic cells and prokaryotic cells.

The term "automated biological sample preparation apparatus" or "automated biological sample preparation system" as used herein refers to commercially available automated apparatus for nucleic acid extraction, particularly those that employ magnetic bead technology.

Unless defined otherwise, all technical and scientific terms used herein have the same meaning as commonly understood by one of the ordinary skill in the art to which this invention belongs. The singular forms "a", "and", and "the" are used herein to include plural referents unless the context clearly dictates otherwise.

Existing automated nucleic acids extraction apparatus isolates or extracts nucleic acids with the aid of magnetic beads, in which nucleic acids released from the lysed biological samples are adsorbed onto the silica coated outer surface of the magnetic beads allowing the nucleic acids to be easily separated or extracted from the sample For the purpose of thorough mixing, a magnetic rod is used to move up and down in the sample vial to stir and mixed the content in the sample well. However, this mixing act per se inevitably causes the splash of the biological sample, leading to cross-contamination, and consequently an erroneous result. Accordingly, existing automated nucleic acids extraction apparatus is designed to operate in a relatively larger volume sample, so as to keep the fluctuation of the liquid surface in the sample well to the minimum.

To solve the cross-contamination problem described above in the existing art, the present invention provides a novel design of a sonic homogenizing module, suitable for use in any of the existing automated nucleic acids extraction apparatus. Instead of having the magnetic rod moving upward and downward in the mixing well for thoroughly mixing, the present sonic homogenizing module uses high frequency sonic waves or ultrasonic waves to gently mix or stir the content in the sample well. Accordingly, the sonic homogenizing module of present invention effectively prevents the cross-contamination by reducing the liquid surface fluctuation to the minimum, further, by help suspending the magnetic beads in the sample, thereby increases the contact between the magnetic beads and the samples, which leads to the enhancement of magnetic beads capturing the nucleic acids.

Figure 1B:
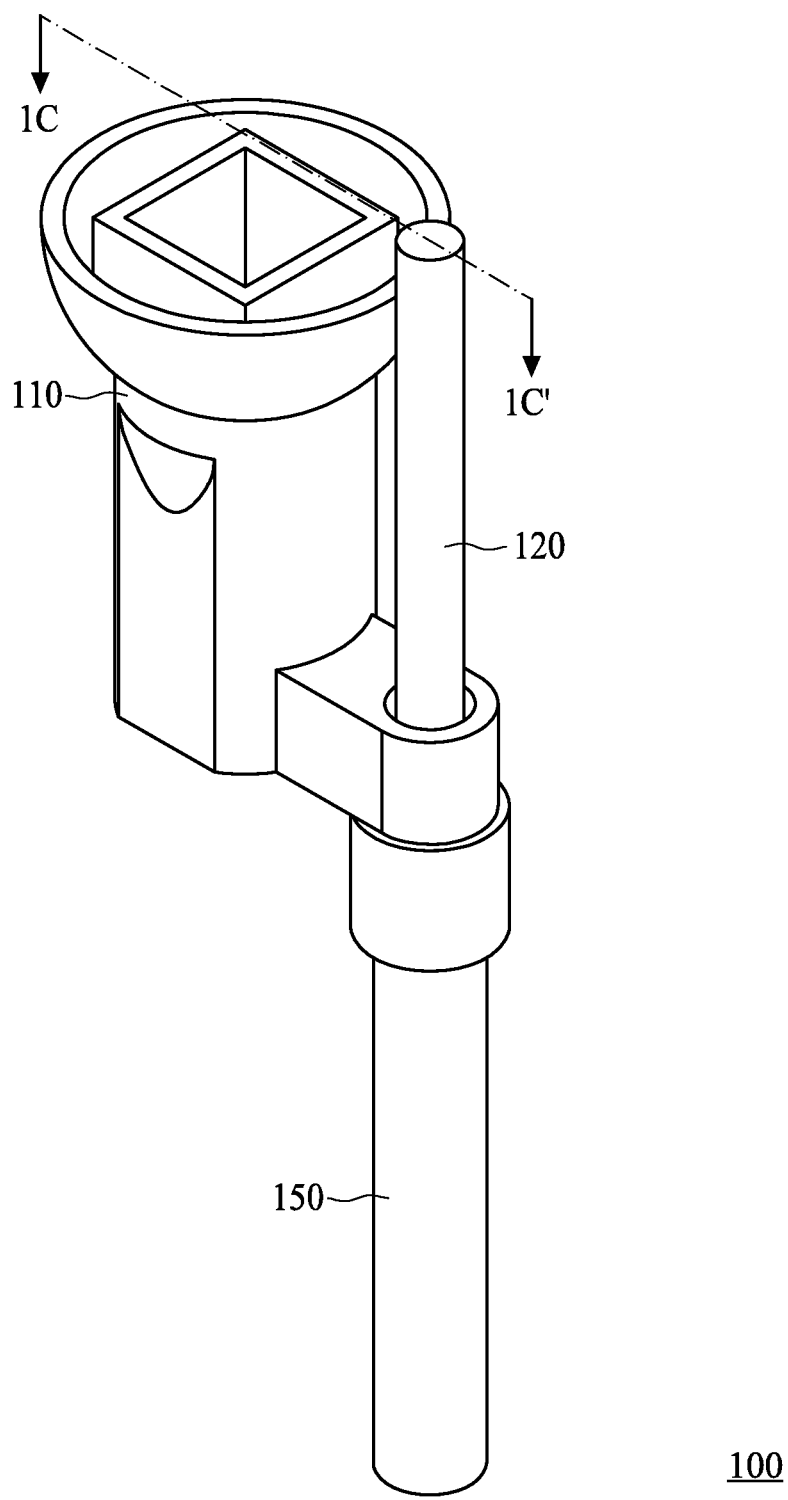
Figure 1C:
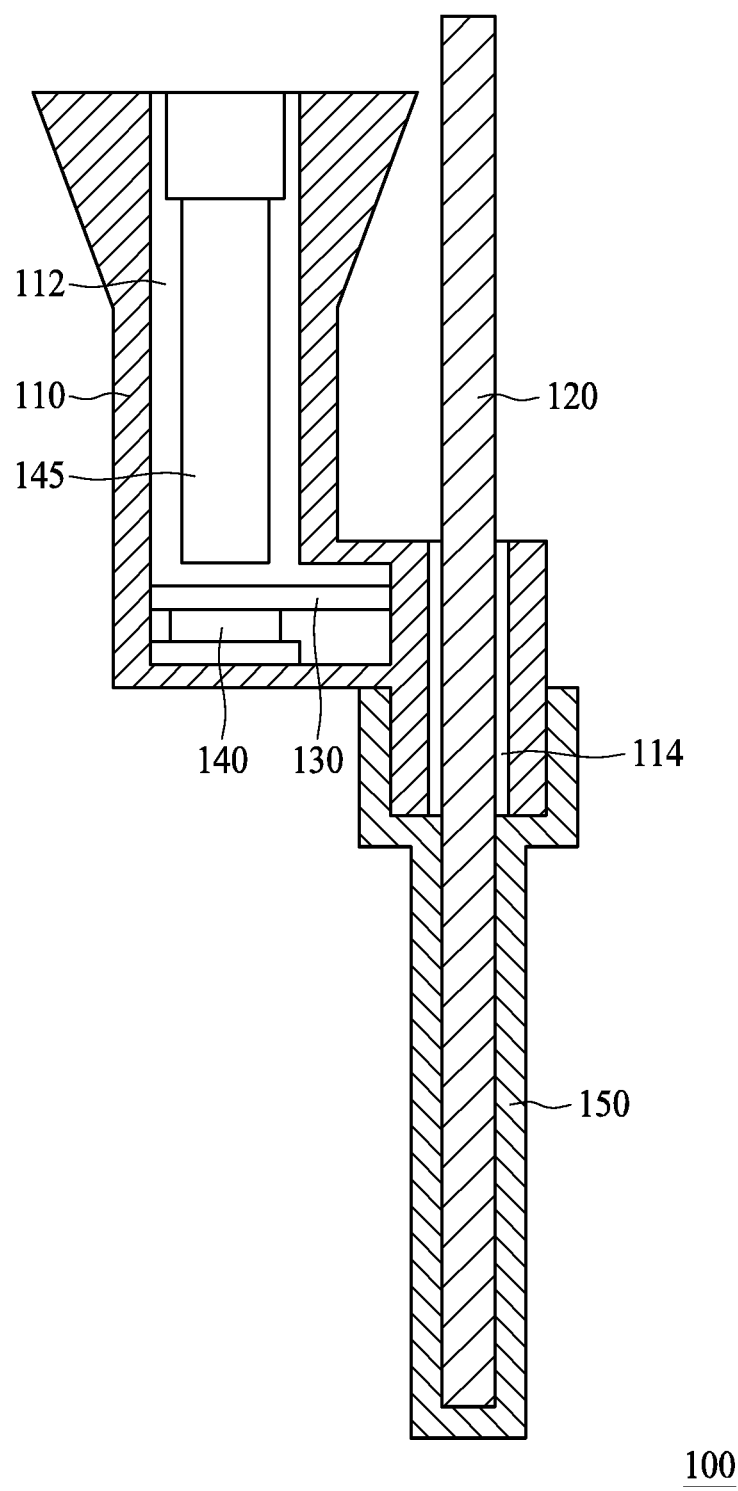
FIG. 1C is a cross-sectional view of the homogenizing module 100 along the line 1C-1C' in FIG. 1B.

References are made to FIGS. 1A to 1C, in which FIG. 1A and FIG. 1B are schematic diagrams respectively depicting a sonic homogenizing module 100 of the present disclosure before and after assembling with a sleeve 150; and FIG. 1C is a cross-sectional view of the homogenizing module 100 of FIG. 1B along the line 1C-1C'.

Structurally, the sonic homogenizing module 100 of present invention has a sleeve-coupling member 110, a rod 120 made of a magnetic material, a piezoelectric conductor 130, and a driver 140 (not visible from FIGS. 1A and 1B) for driving the piezoelectric conductor 130 to produce a sonic vibration for treating a biological sample housed in a sampling well of a biological sample preparation system (note that not the sample well and the biological sample preparation system are not depicted in FIG. 1). It should be noted that the present sonic homogenizing module 100 may be used with any commercially available biological sample preparation system (e.g., automated nucleic acids extraction apparatus) that requires to perform a mixing and/or stirring action during operation.

As illustrated in FIG. 1C, the sleeve-coupling member 110 has a first portion and a second portion, in which the first portion defines a space 112 for coupling with a biological sample preparation system (e.g., the conventional automated nucleic acid extraction system), and for accommodating the piezoelectric conductor 130 and the driver 140 therein; and the second portion comprises a conduit 114 for receiving the magnetic rod 120 therethrough. The present sonic homogenizing module 100 may be coupled to a biological sample preparation system through the engagement with a gripper module commonly used in a biological sample preparation system, in which the gripper module is received or housed in the space 112 of the first portion of the sleeve-coupling member 110. For exemplified purpose, a slot 145 (as depicted in FIG. 1C) may be used to lock the gripper module (not depicted in the figure) tightly in place in the space 112. Any structures and/or configurations suitable for securely locking the gripper module in the space 112 of the sleeve-coupling member 110 may be used in the present disclosure, such structures and/or configurations are thus encompassed within the spirit of the present disclosure.

To prevent cross-contamination problem described above, the present module 100 employing sonic waves or ultrasonic waves to mix or stir the content in a sampling well of a biological sample preparation system. Accordingly, a driver 140 and a piezoelectric conductor 130 are placed in the second space 113 of the first portion of the sleeve-coupling member 110, in which the driver 140 is electrically couple to the piezoelectric conductor 130 and to drive the piezoelectric conductor 130 to produce a sonic and/or ultrasonic vibration at a desired frequency. According to embodiments of the present disclosure, the sonic vibration produced by the piezoelectric conductor 130 of the present sonic homogenizing module 100 has a frequency from 100 KHz to 1,000 KHz (i.e., 1 MHz), such as 100, 101, 102, 103, 104, 105, 106, 107, 108, 109, 110, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1,000 KHz.

Optionally or alternatively, a sleeve (or an overtube) 150 may be fitted on and around the outer surface of the magnetic rod 120 extending out of the conduit 114 of the second portion of the sleeve-coupling member 110. During operation, the sonic vibration produced by the piezoelectric conductor 130 is transmitted to the content (e.g., the magnetic beads and/or molecules (e.g., nucleic acids)) in a sampling well through the sleeve 150 fitted on and around the outer surface of the magnetic rod 120, so as to thoroughly mixed the content in the sampling well. In general, the sleeve 150 is disposable, and is removed once the mixing in each sampling well (or groups of sampling wells) is completed, and a new or un-used sleeve 150 will be fitted on and around the outer surface of the magnetic rod 120 before the gripper module moves the sonic homogenizing module 100 to its next position.

Referring again to FIG. 1C, in some cases, the piezoelectric conductor 130 is disposed in the space 112 of the first portion of the sleeve-coupling member 110 in a manner that it is adjacent to the conduit 114 of the second portion of the sleeve-coupling member 110. It should be noted that, the piezoelectric conductor 130 is not in direct contact with the magnetic rod 120. Further, the sonic vibration generated by the piezoelectric conductor 130 is transmits through the magnetic rod 120, the sleeve 150, and eventually reaches the content in the sampling well, thereby producing the mixing and/or stirring effect.

Figure 2A:
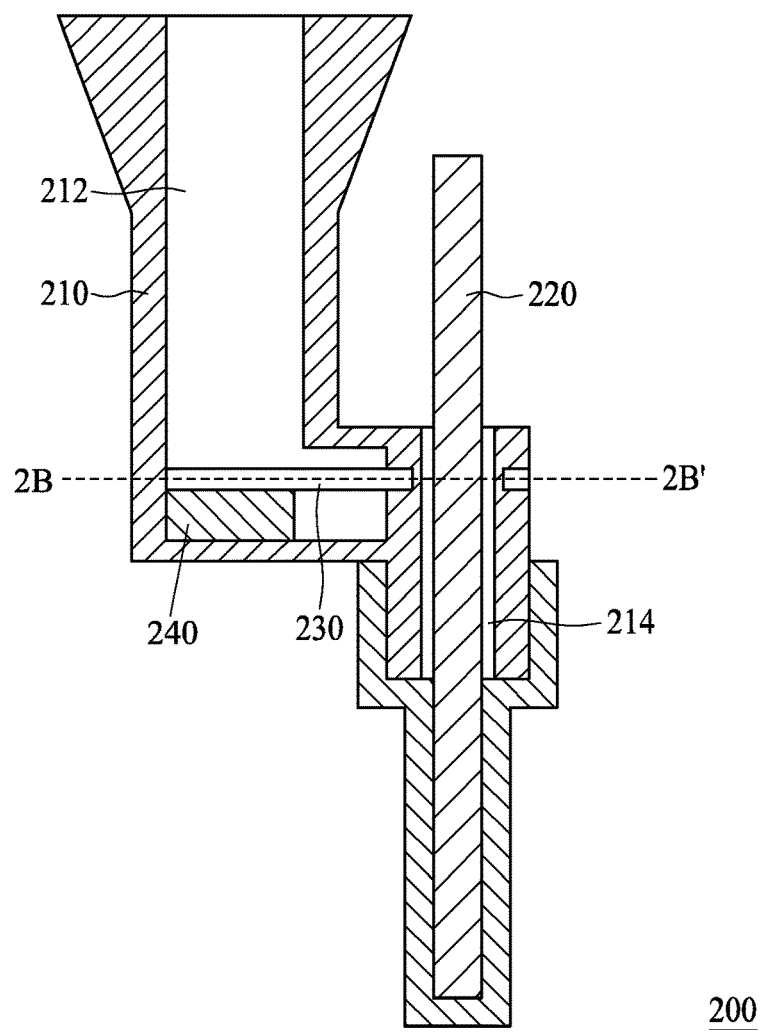
FIG. 2A is a cross-sectional view depicting the interior of a sonic homogenizing module 200 according to another embodiment of the present disclosure.
Figure 2B:
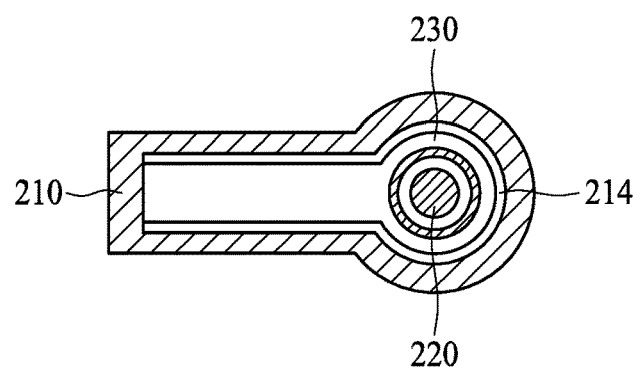
FIG. 2B is a cross-sectional view along the line 2B-2B' of FIG. 2A.

FIG. 2A is a schematic diagram similar to FIG. 1C, in which the components of the sonic homogenizing module 200 are same as those in the module 100 depicted in FIG. 1, except in this case, the piezoelectric conductor 230 disposed in the first portion of a sleeve-coupling member 210 extends into the second portion of the same member 210; and FIG. 2B is a cross-sectional view along the 2B-2B' line in FIG. 2A. In this embodiment, the piezoelectric conductor 230 and driver 240 are disposed at the bottom of the space 212 of the sleeve-coupling member 210, and the piezoelectric conductor 230 is disposed laterally into the second portion and encircles or surrounds the conduit 214, so as to enhance the transmit efficiency of the sonic vibration.

Figure 3:
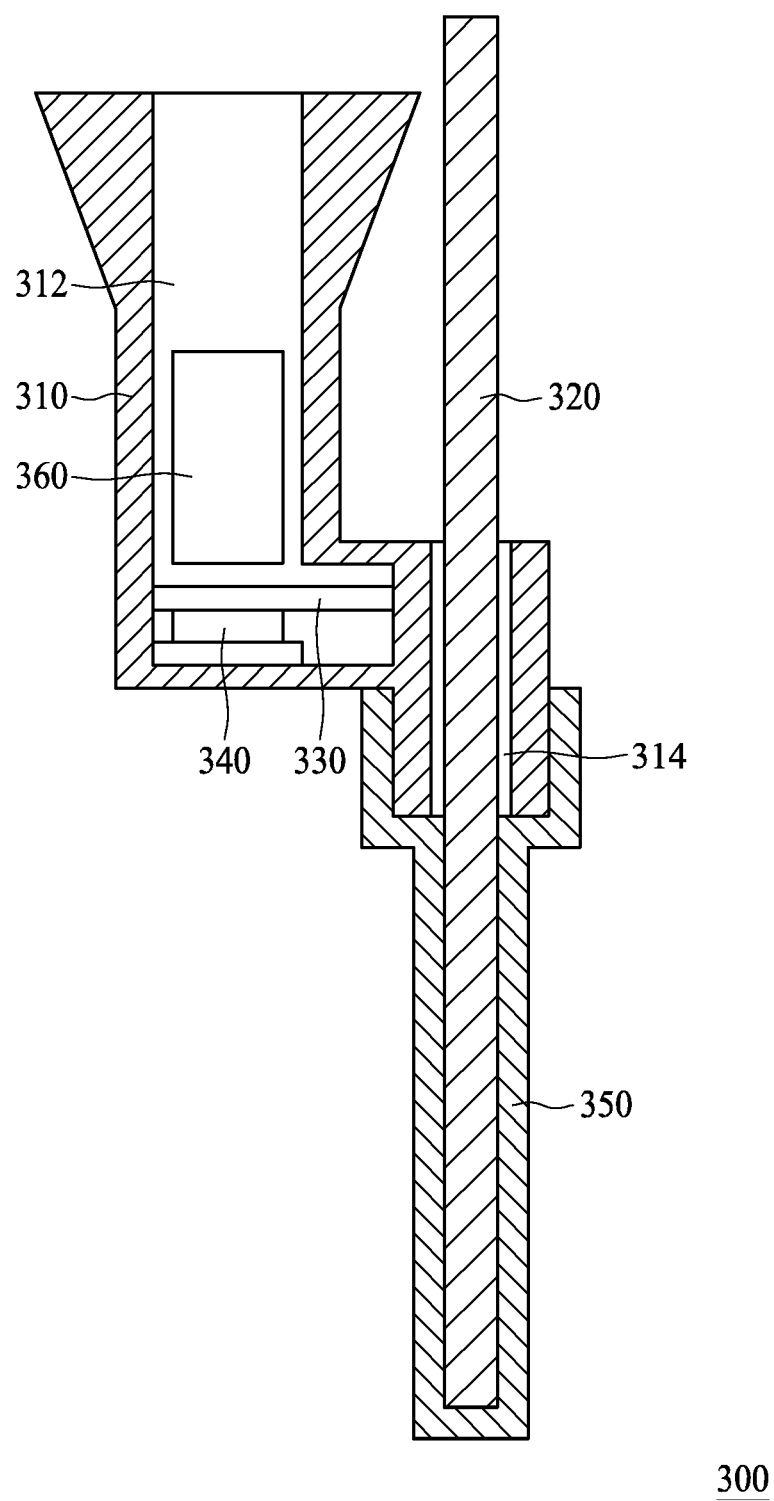
FIG. 3 is a schematic diagram illustrating a sonic homogenizing module 300 in according with another embodiment of the present disclosure.

FIG. 3 is a schematic diagram depicting a sonic homogenizing module 300 in according with another embodiment of the present disclosure. In this embodiment, besides a piezoelectric conductor and a driver as those described in FIGS. 1 and 2, an additional vibration motor 360 is included in the module 300 to aid vibration. Again, the components in the sleeve-coupling member 310 are same as those described above in FIGS. 1 and 2, and their descriptions are omitted for the sake of brevity. The additional vibrational motor 360 is also disposed in the first portion of the sleeve-coupling member 310, particularly in the space 312 and is above or adjacent to both the piezoelectric conductor 330 and the driver 340; the three members (330, 340, and 360) are electrically coupled to each other to produce vibration, either independently or in cooperation. During operation, the user may choose specific vibration component, that is, the vibration motor 360 or the combination of the piezoelectric conductor 330 and the driver 340, in accordance with the specific need of the treatment. Alternatively, both the vibration motor 360 and the combination of the piezoelectric conductor 330 and the driver 340 may be used to generate vibration. Furthermore, the skill artisan may change or modify the configuration of the vibration components (i.e., the piezoelectric conductor 330/the driver 340, and the vibration motor 360) according to the actual need. In one non-limiting embodiment, the driver 340 is disposed outside the sleeve-coupling member 310.

Figure 4:
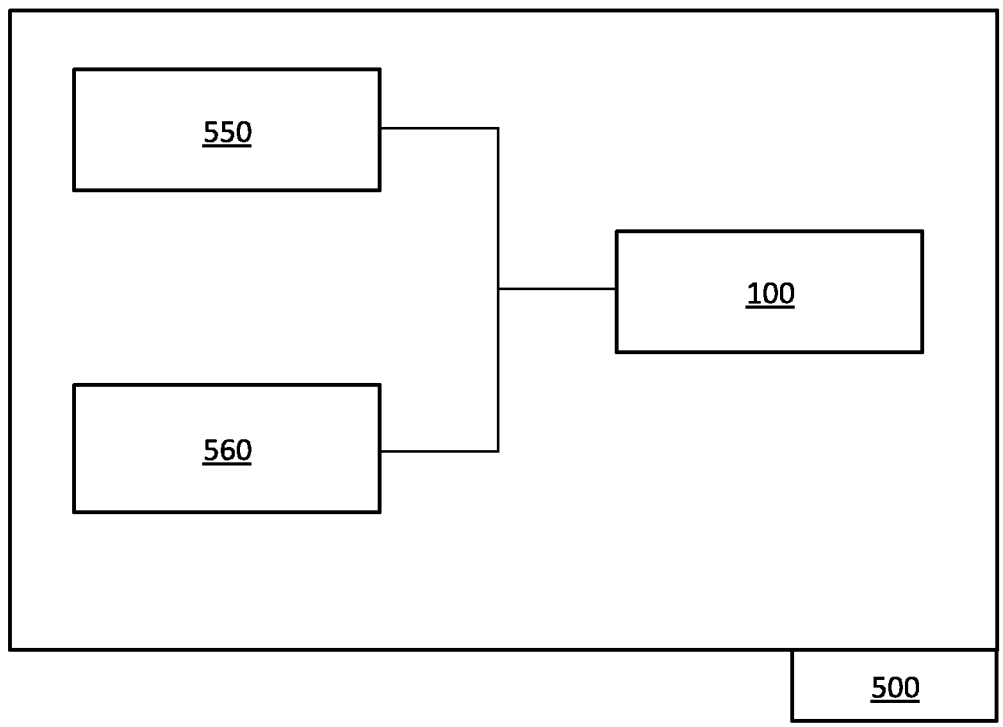
FIG. 4 is a block diagram depicting the layout of a typical biological sample preparation system 500 in according with one embodiment of the present disclosure.

FIG. 4 is a schematic diagram illustrating the layout of a typical biological sample preparation system 500 in according with one embodiment of the present disclosure. The biological sample preparation system 500 typically comprises a power supply 550, a gripper module 560 and at least one of a sonic homogenizing module, such as the sonic homogenizing module 100, 200 or 300 in the present disclosure. In this particular embodiment, the sonic homogenizing module is the sonic homogenizing module 100 depicted in FIGS. 1A to 1C. Specifically, the power supply 550 is electrically couple to the gripper module 560 to provide electrical power for operating the biological sample preparation system 500; the gripper module 560 may be an automated robotic arm that can grip and hold the sonic homogenizing module 110 of the present invention in place, and move horizontally and/or vertically until it reaches its next operation position. Moreover, the gripper module 560 may further includes an actuator (not shown) for driving the magnetic rod 120 to move in a linear up-and-down motion.

Figure 5:
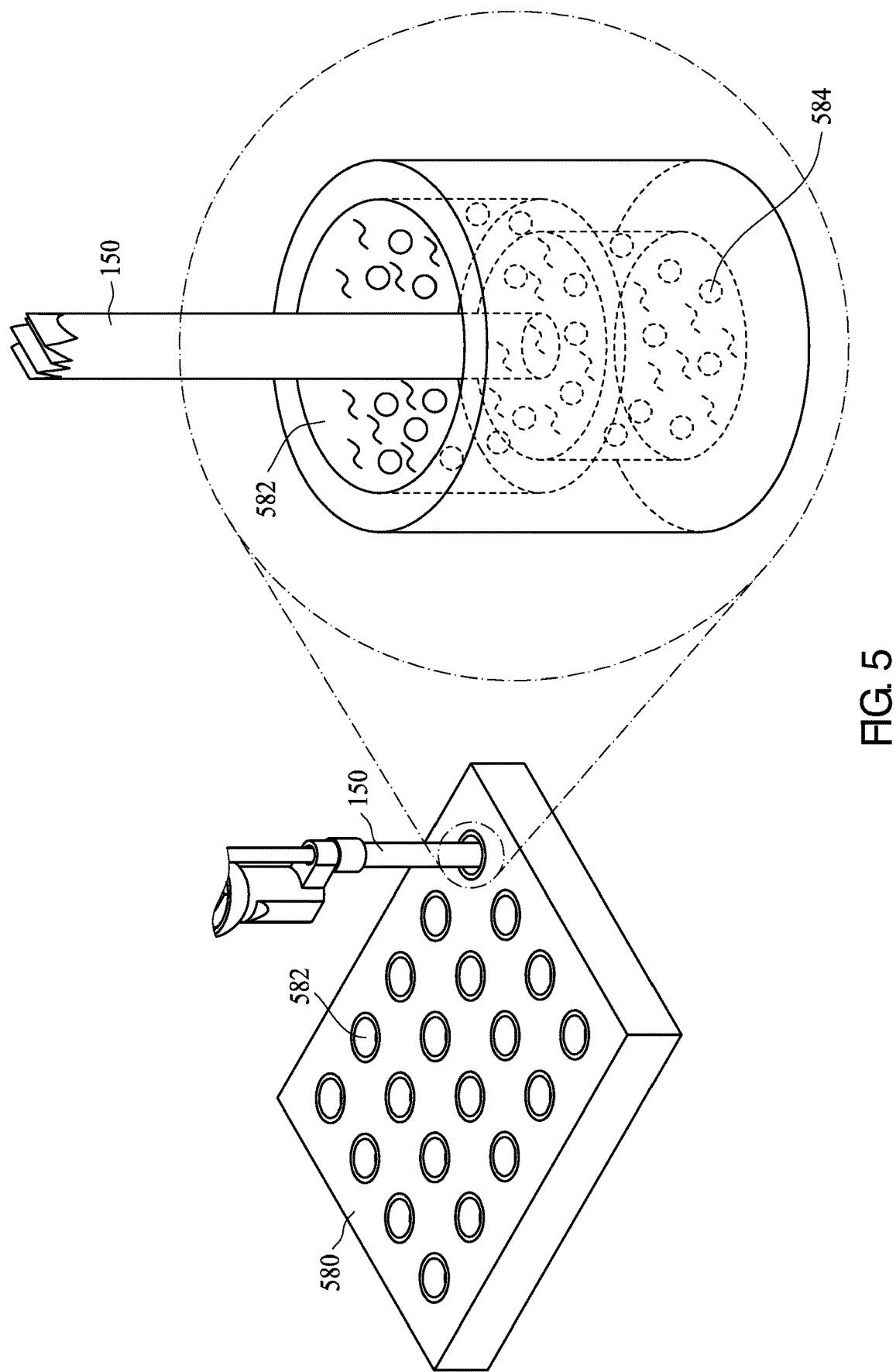
FIG. 5 is a schematic diagram illustrating the operation of the sonic homogenizing module 100 in according with one embodiment of the present invention.

Reference is now made to FIG. 5, which depicts how a biological sample preparation system operates. In general, a gripper module (e.g., an automated robotic arm, not visible from FIG. 5) moves a sonic homogenizing module, such as the sonic homogenizing module 100, to a designated position (e.g., above a sampling well 582 of a sample plate 580), in which the magnetic rod 120 having fitted with a sleeve 150 on and around its outer surface is moved downwardly into the well 582, and then, a vibration motor and/or the combination of a piezoelectric conductor and a driver is deployed to generate ultrasonic wave that got transmitted through the magnetic rod, the sleeve and into the sampling well 582, and causes the content 584 (i.e., magnetic beads and the lysed biological sample) to be mixed. Thus, opposite to the conventional manner, in which the mixing is achieved by moving a rod up-and-down continuously in the sampling well for certain period of times, which causes the liquid to fluctuate and spills over to other sampling wells; the present invention achieves mixing via keeping the magnetic rod in a static position below the liquid surface, and accomplishes mixing via sonic vibration. By this manner, a biological sample preparation system comprising the present sonic homogenizing module may extract nucleic acids in lesser amount or volume of sample, while reducing the risk of cross-contamination.

The skill artisan may understand that the wells in the sample plate may be filled with different agents according to the actual needs in the process of biological sample preparation. For example, each well is filled with magnetic beads, a lysis buffer, a binding buffer, a wash buffer and/or an eluate buffer, in addition to a biological sample.

Furthermore, the biological sample preparation system 500 may comprise multiple sonic homogenizing modules 100 arranged in a side-by-side manner, and each sonic homogenizing module 100 is couple to a gripper module, so that multiple extractions may be conducted simultaneously.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A sonic homogenizing module for use with a biological sample preparation system comprising a gripper module, the sonic homogenizing module comprises:
   a rod made of a magnetic material;
   a piezoelectric conductor;
   a driver; and
   a sleeve-coupling member having
      a first portion defining a space for coupling with the gripper module of the biological sample preparation system, and for accommodating the piezoelectric conductor and the driver therein; and
      a second portion having a conduit for receiving the rod there through;
   wherein
   the driver is electrically coupled with the piezoelectric conductor and is configured to drive the piezoelectric conductor to generate a sonic vibration.

2. The sonic homogenizing module of claim 1, wherein the sonic vibration generated by the piezoelectric conductor has a frequency between 100 KHz to 1 MHz.

3. The sonic homogenizing module of claim 1, further comprising a motor disposed in the space of the first portion.

4. The sonic homogenizing module of claim 1, wherein the piezoelectric conductor is disposed in a manner to be adjacent to the conduit.

5. The sonic homogenizing module of claim 1, further comprising a sleeve removably fitted on and around the outer surface of the rod extending out of the conduit of the second portion of the sleeve-coupling member.

6. The sonic homogenizing module of claim 5, wherein the sonic vibration generated by the piezoelectric conductor is transmitted through the sleeve fitted on and around the outer surface of the rod.

7. The sonic homogenizing module of claim 1, wherein the space of the first portion extends into the second portion of the sleeve-coupling member.

8. The sonic homogenizing module of claim 1, wherein the piezoelectric conductor accommodated in the space of the first portion is disposed in a manner that it surrounds the conduit of the second portion.

9. A biological sample preparation system, comprising:
   the sonic homogenizing module of claim 1; and
   a gripper module electrically coupled with the driver of the sonic homogenizing module of claim 1 and configured to move the sonic homogenizing module of claim 1.

10. The biological sample preparation system of claim 9, further comprising a sleeve, which is removably fitted on and around the outer surface of the rod extending out of the conduit of the second portion of the sleeve-coupling member.

11. The biological sample preparation system of claim 10, further comprising a sample plate, wherein the sample plate comprises a plurality of wells, and the gripper module is configured to move and insert the rod having the sleeve fitted on and around its outer surface into at least one of the plurality of wells and stayed at its position for homogenization.

* * * * *